United States Patent [19]
Doppelfeld et al.

[11] Patent Number: 4,808,529
[45] Date of Patent: Feb. 28, 1989

[54] ENZYMES IMMOBILIZED ON POLYAMIDES OR CELLULOSE HYDRATE

[75] Inventors: Peter Doppelfeld, Leverkusen, Fed. Rep. of Germany; Gary Oosta, Elkhart, Ind.; Alexander Riebel, Leverkusen; Karl-Wilhelm Schranz, Odenthal, both of Fed. Rep. of Germany

[73] Assignee: Miles Inc., Elkhart, Ind.

[21] Appl. No.: 832,230

[22] Filed: Feb. 24, 1986

[30] Foreign Application Priority Data

Mar. 13, 1985 [DE] Fed. Rep. of Germany ....... 3508908
Aug. 14, 1985 [DE] Fed. Rep. of Germany ....... 3529094

[51] Int. Cl.$^4$ .................... C12N 11/12; C12N 11/08; C12Q 1/32; C12Q 1/28
[52] U.S. Cl. ..................... 435/179; 435/14; 435/25; 435/26; 435/28; 435/177; 435/180; 435/182; 435/288
[58] Field of Search ............... 435/174, 177, 179, 180, 435/182, 288, 14, 25, 26, 28

[56] References Cited

U.S. PATENT DOCUMENTS 3,705,084 12/1972 Reynolds ........................... 435/180
4,231,754 11/1980 Vogelhut ......................... 435/14 X

OTHER PUBLICATIONS

Zaborsky, O., Immobilized Enzymes, CRC Press, Cleveland, Ohio, 1973, pp. 79-82.
Olson et al., Immobilized Enzymes in Food and Microbiol Processes, Plenum Press, N.Y., 1974, pp. 63-69.

Primary Examiner—David M. Naff
Attorney, Agent, or Firm—Roger N. Coe

[57] ABSTRACT

Proteins such as enzymes are attached directly to a polyamide or cellulose hydrate carrier. Attachment can be carried out by impregnation of the carrier with a protein solution. The carrier can be in the form of a membrane, and the polyamide can be nylon. Resulting carrier-bound proteins find utility as biocatalyst, as test strips or as chromatography materials. In a preferred embodiment, a polyamide or cellulose hydrate membrane carrier is impregnated with an enzyme selected from peroxidase, glucose oxidase, diaphorase and glucose dehydrogenase and then dried, coated with a luminol solution and again dried. The resultant membrane can be used for glucose determination by measuring chemiluminescence produced when the membrane contacts a glucose solution.

1 Claim, No Drawings

ENZYMES IMMOBILIZED ON POLYAMIDES OR CELLULOSE HYDRATE

The invention relates to proteins bound to polyamides or cellulose hydrate and to a process for the preparation of these carrier-bound proteins. The carrier-bound proteins can, for example, be used for the preparation of biocatalysts, chromatography materials or test strips. For the preparation of test strips the carriers are particularly suitable in the form of films or membranes.

As is known, test strips are frequently used in order to determine, semi-quantatitively or quantitatively, certain compounds, such as, for example, glucose, albumin, bilirubin, urobilinogen, nitrite, ketonic bodies and the like in liquids in a simple and rapid manner. In general, the liquids are biological fluids, such as, for example, urine, blood, serum, plasma or liquor, but also beverages or effluents.

A large number of carrier materials which are used for the preparation of test strips are known.

Thus, for example, enzymes and other reagents are introduced into absorbent paper by impregnation, or swellable, natural or specially prepared polymers or latices are used, complicated, multi-layer assemblies being used occasionally in order to protect the sensitive enzymes from the harmful affects of other chemicals present in the layers.

Fine-pored membranes composed of various polymers, such as, for example, polyethylene, polyvinyl chloride or other high-molecular compounds or mixtures thereof, which are either porous themselves or are prepared in an "open-pored" state by adding filling materials, such as gypsum, kieselguhr, silica gel or the like, are also described as absorption materials for the enzymes.

A so-called distribution layer which is intended to effect the most uniform possible distribution of the test liquid on the reaction surface is additionally described in some use examples. These distribution layers usually consist of prefabricated glass or polymer particles of a specific size, which are then glued to the surface by means of a binder. The necessary cavities for the absorption and distribution of the test liquid are thus formed. Distribution layers which consist of insoluble fibres or nonwovens and hence fulfil the same purpose are also described instead of those consisting of particles.

Finally, special membranes composed of polyamide (nylon 66) which have been rendered hydrophilic and carry on their surface functional groups, such as, for example, carboxyl groups or amino groups, are described in European Patent Application No. 83 30 05 17.6.

The use of these membranes for immobilising enzymes after prior chemical modification is also described in this reference. One modification is the attachment of Cibachrom Blue ° to the membrane. As is known from the literature, this dyestuff is capable of binding enzymes which are dependent on NAD in a highly specific manner. It is demonstrated by means of lactate dehydrogenase in Example 5 of this application that the attachment is only effected via the dyestuff.

The second process mentioned in this application is the covalent attachment of alkaline phosphatase to the membrane by means of glutaraldehyde.

It has now been found, surprisingly, that polyamides and also cellulose hydrate are capable, without prior chemical modification, of binding proteins. The binding is effected direct to the carrier. Hydrophilic carriers are preferred, since they are more easily wetted, and the application of the proteins is thereby facilitated. Porous carriers have a larger surface and facilitate the diffusion of, for example, substrates; they ar therefore preferred.

The starting polymers used for the carriers according to the invention are polyamides insoluble in alcohol and having a ratio of $CH_2$ to $NHCO$ groups within the range from 5:1 to 7:1. Polyhexamethylene sebacamide (nylon 610), poly-$\epsilon$-caprolactam (nylon 6) and polyhexamethylene adipamide (nylon 66) having a molecular weight $>30,000$ are preferred.

The process of rendering hydrophilic and the introduction of functional groups are effected by coagulating a mixed solution of the polyamide and the polymer ($MW > 10,000$) containing the functional groups in formic acid, nuclei being first formed by the controlled addition of a non-solvent (for example water). The final precipitation is then effected after the solution has been applied to a substrate by immersing the latter in a precipitation bath consisting of definite amounts of solvent and non-solvent. The membrane thus prepared is washed with water and dried.

Functional groups, such as, for example, carboxyl groups, amino groups, sulphonic acid groups, imino groups, thio groups, hydroxyl groups, pyridyl groups or phosphoryl groups or derivatives thereof can influence the binding of the proteins. This provides a possible means of selectively binding certain proteins. The functional groups can also be present in an "activated" form. "Activated" groups are to be understood as meaning, in a chemical sense, groups which are "activated" by the introduction of a substituent, such as, for example, halogen, phenyl, carboxyl or sulphonyl, that is to say the substituents have the effect of rendering the molecule more positive, which expresses itself in an increased acidity of the methylene or carboxyl H atom located in the $\alpha$-position relative to the central atom. The introduction of substituents in the $\alpha$-position can be effected by methods which are known in organic chemistry.

It has also been found that the "activation" of the functional groups has an effect on the binding properties of the carriers and, in particular, on the selectivity of the attachment. For the preparation of test strips, the carriers are preferably employed in the form of films or membranes. The proteins immobilised on the carrier are normally biologically active proteins, such as, for example, enzymes, receptors, antigens or antibodies. The proteins are preferably applied to the carrier in the form of solutions. Impregnation processes, such as, for example, dipping the carrier into the protein solution or coating the carriers with the protein solution are particularly preferred. The coating is particularly suitable for the mechanised processing of carriers in the form of films or membranes. The proteins attach themselves firmly to the carrier and can no longer be removed by washing. The firm binding of the proteins makes it possible to carry out multiple coatings without proteins located on the carrier being washed off. In addition, the firm binding of the proteins to the carrier offers the possibility of employing these proteins as biocatalysts. Multi-layer assemblies are also possible, especially for test strips. As can be seen from the examples, it is possible to prepare test strips in which different conditions suited to the particular reaction prevail in the various layers. It is therefore possible in this way to prepare a test strip for the determination, described in U.S. Pat. No. 4,231,754, of glucose by means of luminol without complicated and expensive multi-layer systems containing separating layers and/or substances which alter the layer pH being required.

An important advantage of the carriers, especially as films or membranes for the preparation of test strips, is tensile strength. In addition, the carriers hardly swell and they exhibit a very substantially homogeneous surface, which facilitates evaluation, particularly using reflection photometers.

EXAMPLES

Examples 1 to 4 illustrate the binding of enzymes to the carriers. For this, pieces of membrane each measuring 5×5 cm (see Table 1) were immersed in an enzyme solution for 30 minutes and were thus impregnated. The membranes were then washed in 3 times 500 ml of water for 20 minutes in each case in order to remove unbound enzyme. The bound enzymes were detected via their catalytic activity. This was effected by preparing test solutions containing the reagents required for the detection of activity and incubating pieces measuring 1×1 cm of the membranes charged with enzymes therein. After 30 minutes the extinction of the test solutions was measured in a spectral photometer (Beckmann DU-6 ®).

As a control, untreated membranes were included in each case and the extinctions of the corresponding test solutions were taken into the calculation as a blank value.

Examples 5 to 9 describe the preparation of test strips.

TABLE 1

| No. | Membrane |
|---|---|
| (1) | A polyurethane membrane prepared by coating a solution of 13.3 g of polyurethane together with 66.37 ml dimethylformamide (DMF), with the addition of 7.24 g of a cationic polyurethane dispersion in DMF/water and 0.07 g of sodium laurylsulphate and 11.01 g of titanium dioxide, onto a polyester film, followed by coagulation. |
| (2) | A porous polyester membrane (Nuclepore ®) |
| (3) | As membrane 1, without the addition of the cationic polyurethane dispersion but with the addition of 0.05 g of ethoxylated nonylphenol |
| (4) | As membrane 1, with the addition of 0.05 g of ethoxylated nonylphenol |
| (5) | Polyamide 66 having activated carboxyl groups on the surface |
| (6) | Membrane composed of cellulose hydrate (CUPROPHAN ® made by ENKA) |
| (7) | Polyamide 66 without functional groups |
| (8) | Isotropically foamed polyamide 66 having carboxyl and amino groups on the surface. Pore size 0.5 μm |
| (9) | As membrane 8, but pore size 0.2 μm |

EXAMPLE 1

Enzyme solution: 5 mg of peroxidase (47 U/mg, Miles, USA) in 20 ml of water.
Test solution:
2.2 ml of H$_2$O$_2$ (13% strength)
6.2 mg of 4-aminoantipyrine
115.0 mg of sodium dichlorobenzenesulphonate
90 ml of water
10 ml of phosphate buffer (0.5 mol/l, pH 7.0)

| Membrane | Results: Extinction at 505 nm |
|---|---|
| 1 | +0.063 |
| 2 | +0.088 |
| 3 | +0.117 |
| 4 | +0.048 |
| 5 | +0.728 |
| 6 | +0.140 |
| 7 | +0.043 |
| 8 | +0.025 |
| 9 | +0.032 |

EXAMPLE 2

Enzyme solution: 5 mg of glucose oxidase (250 U/mg, Boehringer, Mannheim) in 20 ml of water
Test solution:
540 mg of glucose
10 mg of peroxidase (47 IU/mg)
6.2 mg of 4-aminoantipyrine
115.2 mg of sodium dichlorobenzenesulphonate
90 ml of water
10 ml of phosphate buffer (0.5 mol/l, pH 7.0)

| Membrane | Results: Extinction at 505 nm |
|---|---|
| 1 | +0.013 |
| 2 | −0.071 |
| 3 | −0.016 |
| 4 | −0.084 |
| 5 | +0.18 |
| 6 | +0.221 |
| 7 | +0.063 |
| 8 | +0.594 |
| 9 | +0.574 |

EXAMPLE 3

A selection of the abovementioned membranes was used for the further tests.
Enzyme solution: 5 mg of diaphorase (53 U/mg, Boehringer, Mannheim) in 20 ml of water
Test solution:
0.05 g of 2-p-iodophenyl-3-p-nitrophenyl-5-phenyltetrazolium chloride×H$_2$O (INT) was dissolved by heating in 5 g of 20% strength aqueous polyvinylpyrrolidone solution (PVP).
0.05 g of NAD+
0.01 g of glucose dehydrogenase (61.5 IU/mg; made by Biocentrics)
180 mg of glucose
60 ml of water
20 ml of HEPE's buffer (0.1 mol/l, pH 7.2)

| Membrane | Results Extinction at 500 nm |
|---|---|
| 9 | +0.195 |
| 5 | +0.333 |
| 6 | +0.32 |

EXAMPLE 4

Enzyme solution: Glucose dehydrogenase (61.5 U/mg) in 20 ml of water
Test solution:
0.05 g of INT were dissolved by heating in 5.0 g of 20% strength PVP solution 180 mg of glucose
0.05 g of NAD+
0.01 g of diaphorase (53 U/mg)
60 ml of water
20 ml of HEPE's buffer (0.1 mol/l; pH 7.2)

| Membrane | Results: Extinction at 500 nm |
|---|---|
| 9 | +0.23 |
| 5 | +0.061 |
| 6 | +0.163 |

Examples 1 to 4 show that carriers composed of polyamide or cellulose hydrate are suitable for the direct binding of proteins. In this respect, membranes having different surface properties exhibit a certain selectivity in the binding of the enzymes.

EXAMPLE 5

Examples 5 and 6 illustrate multi-layer glucose strips prepared by known methods. They serve as a proof of the fact that unsatisfactory products are obtained thereby.

With the aid of a suitable coating and drying device such as is used for the preparation of photographic single-layer and multi-layer materials, the following coating solution was applied to a carrier made of polyester film: 0.25 g of luminol (made by Merck) is dissolved, together with 0.1M tetrasodium ethylenediaminetetracetate (Trilon B ®), in 25 ml of water, 125 g of 20% strength gelatin gel in 350 ml of water were melted at 40° C. and the pH of the resulting solution was brought to a value of 9.7 by means of the appropriate amount (approx. 20 ml) of 50% strength Trilon B ® solution. The wet coating was 170 μm, which corresponds to an amount of gelatin of approx. 7.0 g/m$^3$ and an amount of luminol of approx. 0.07 g/m$^3$.

After drying, a second layer was applied over the first; this was coated from the following coating solution:

0.3 g of 75% strength dodecylbenzenesulphonate (DBS paste) was dissolved in 3 ml of chloroform and 2 ml of 7.5% strength polycarbonate (Makrolon) solution containing chloroform; 0.123 g of glucose oxidase (250 IU/mg) and 0.616 g of peroxidase (47 U/mg) are dissolved in 3.6 ml of water and dispersed, with vigorous shaking, in the solution prepared above. 23 ml of a 13.2% strength dispersion of an aqueous polyacrylamide solution in chloroform were combined with 27 ml of a 7.5% strength solution of Makrolon in chloroform, and mixed with the enzyme-containing dispersion.

This solution was applied at a thickness of 70 μm to the luminol-containing gelatin layer and was dried at room temperature. If a sample of 30 microliters of a solution of 250 mg of glucose in 100 ml of water is applied to the finished layer assembly, a chemiluminescence appears in accordance with the known reaction.

After the layer assembly has been stored for a period of about 14 days at room temperature, the glucose oxidase has been destroyed to such an extent that the chemiluminescence only appears if a small amount of glucose oxidase solution is applied to the test strip before the addition of the glucose solution.

In this test system the glucose oxidase is not firmly bound in the second layer.

In addition, the reaction leading to the chemiluminescence only takes place if the samples applied are distributed by means of filter paper or a similar absorbent material.

EXAMPLE 6

The procedure was as in Example 5, but the following coating solution was used as the second enzyme-containing layer:

125 g of a 20% strength gelatin gel were melted in 100 ml of water at 40° C.

12.5 ml of an aqueous solution of glucose oxidase (1000 IU/ml) and a solution of 1.2 g of peroxidase in 10 ml of water were added to the above gelatin solution, and 1.5 ml of a 4% strength solution of wetting agent were added.

The solution was applied as a wet coating of 70 μm to the dry gelatin layer containing luminol and was dried at 20°-25° C.

No chemiluminescence at all could be observed in this test by moistening with glucose solution.

Here the glucose oxidase is inactivated immediately. The processes described in Example 5 and 6 are thus unsuitable for the preparation of test strips of this type.

Examples 7 to 9 illustrate the suitability of the carriers according to the invention for the preparation of test strips.

EXAMPLE 7

4.5 meters of a web 16 cm wide of the membrane 9 were coated at 70 μm with the following solution and dried at room temperature:

0.61 g of luminol was dissolved by means of 11.3 ml of a 50% strength solution of Trilon B ®, the mixture was poured into 242 ml of water, and a solution of 2.347 g of glucose oxidase and 1.246 g of peroxidase in 23.5 ml of water was then added. The pH of this solution was adjusted to a value of 9.7 with 50% strength Trilon B ® solution.

On applying 10-20 microliters of a solution of glucose in water, a pronounced chemiluminescence was observed, which could be measured by means of an appropriately sensitive photometer.

Instead of the glucose solution, blood samples containing glucose were also applied to the prepared membrane, when chemiluminescence also appeared, but with a lower intensity.

EXAMPLE 8

A piece of web as described in Example 7 was coated with two solutions: first at 70 μm with the following solution:

2.347 g of glucose oxidase and
246 g of peroxidase were dissolved in 296.4 ml of water.

After drying had been carried out at room temperature, a second coating, also at 70 μm, was carried out with the following solution:

0.16 g of luminol were dissolved by means of 11.3 ml of 50% strength Trilon B ® solution in 20.6 ml of water, and the mixture was added to a solution of 150 g of a 20% gelatin gel in 117.5 ml of water. The pH of this solution was adjusted to a value of 9.7 with Trilon B ® solution.

After drying, the membrane thus prepared was treated with glucose solution or blood containing glucose, as described in Example 7, and the resulting chemiluminescence was measured. In comparison with Example 7, a very much stronger chemiluminescence appeared both with glucose solution and with blood containing glucose, and this, as also in the case of Example 7, had hardly decreased in intensity even after the membrane had been stored for several months at room temperature.

EXAMPLE 9

3 ml of the coating solution used in Example 7 were applied by means of a doctor blade to each of pieces of membrane 9 approx. 20 cm long. In separate tests the amount of peroxidase was increased by a factor of 1½ and was also decreased to ¾, ½ and ¼ of the amount used in Example 7.

In evaluating the chemiluminescence produced by means of glucose solution, it was found that the intensity of the chemiluminescence decreased greatly both at a higher amount of peroxidase and at a lower amount of peroxidase than that in Example 7.

The amount of glucose oxidase was also varied in the same way. In contrast with peroxidase, within the scope of the range of quantities used, a direct relation of the amount of enzyme to the intensity of the chemiluminescence was observed with glucose oxidase.

EXAMPLE 10

The following experiment was then carried out in order to obtain information on the nature and strength of the binding to the carrier.

Pieces of membrane measuring 5×5 cm (membrane No. 9) are immersed for 30 minutes in a solution of 5 mg of glucose oxidase in 20 ml of water and are impregnated therewith. The pieces of membrane are then washed for 20 minutes in 3 times 500 ml of water in order to remove excess enzyme.

Pieces of this charged membrane measuring 1×1 cm are then each washed for 15 minutes in 10 ml of sodium chloride solution having a different concentration in each case (0.1M, 0.25M, 0.5M, 1.0M and 3.0M).

The test solution described in Example 2 was used to determine the activities, both the sodium chloride solution and the pieces of membrane themselves being tested, after the removal of the latter.

The evaluation showed that no enzyme activity at all could be detected in the various solutions of sodium chloride, whereas the colour intensities observable in the appropriate pieces of membrane exhibited no significant decrease in the enzyme activity in the membranes. This test shows clearly that the immobilisation of the enzymes is not based on ionic interactions.

Obviously, many other modifications and variations of the inventions as hereinbefore set forth can be made without departing from the spirit and scope of the invention.

What is claimed is:

1. The process for forming a carrier-bound protein which comprises
impregnating a membrane carrier of polyamide or cellulose hydrate having functional groups from the group consisting of carboxyl groups, amino groups, sulphonic acid groups, imino groups, thio groups, hydroxyl groups, pyridyl groups, and phosphoryl groups with an enzyme from the group consisting of peroxidase, glucose oxidase, diaphorase and glucose dehydrogenase,
drying the impregnated carrier,
coating the resulting dried carrier with a luminol solution having an adjusted pH value of 9.7, and then drying the luminol coated carrier.

* * * * *